United States Patent [19]

Hannan, III et al.

[11] 4,299,817

[45] Nov. 10, 1981

[54] HAIR CARE COMPOSITIONS

[75] Inventors: Roy B. Hannan, III, Danbury, Conn.; Errol D. Goddard, Haworth, N.J.; Denise C. Galante, New Rochelle, N.Y.

[73] Assignee: Union Carbide Corporation, New York, N.Y.

[21] Appl. No.: 48,975

[22] Filed: Jun. 15, 1979

Related U.S. Application Data

[63] Continuation-in-part of Ser. No. 827,264, Aug. 24, 1977, abandoned.

[51] Int. Cl.$^3$ .............................................. A61K 7/06
[52] U.S. Cl. .................................................... 424/70
[58] Field of Search .............................. 424/70, 78, 71

[56] References Cited

U.S. PATENT DOCUMENTS

| | | | |
|---|---|---|---|
| 3,715,428 | 2/1973 | Quasius et al. | 424/47 |
| 3,849,548 | 11/1974 | Sheldon | 424/70 |
| 3,958,581 | 7/1976 | Abegg et al. | 424/7 |
| 3,988,438 | 10/1976 | Weinstein | 424/70 |
| 4,009,255 | 2/1977 | Kalopissus et al. | 424/70 |
| 4,009,256 | 2/1977 | Nowak et al. | 424/70 |
| 4,013,787 | 3/1977 | Varlerberghe et al. | 424/70 |
| 4,062,939 | 12/1977 | Scott | 424/70 |

OTHER PUBLICATIONS

*J. Soc. Cos. Chem.*, 19,863–19,880 (Dec. 9, 1968).
*Ind. Eng. Chem.*, 57 (10) 35 (1965).

*Primary Examiner*—Frederick E. Waddell
*Attorney, Agent, or Firm*—Gary L. Wamer

[57] ABSTRACT

Hair care compositions comprising polyelectrolyte complexes have superior hair setting capability for the hair.

7 Claims, No Drawings

HAIR CARE COMPOSITIONS

This application is a continuation-in-part of application Ser. No. 827,264, filed Aug. 24, 1977 now abandoned.

BACKGROUND OF THE INVENTION

This invention relates to hair care compositions. More particularly, this invention relates to wave-set compositions that are especially useful and effective at high humidity levels.

Conventional wave set compositions typically employ a water soluble polymer as the hair setting agent. The polymer functions by depositing a thin resin film on hair which serves to confine the hair to the desired configuration. While relatively effective as a wave setting composition, these conventional compositions possess inherent deficiencies, the most significant of which is their inability to promote improved humidity resistant curl retention while at the same time being easily deposited on the hair or removed from the hair during shampooing. It is generally recognized that the ability of a polymer based composition to impart a humidity resistant curl to the hair is very much dependent on the hygroscopicity, i.e. water sorbing tendency, and the tensile strength of the polymer film. Polymers that are somewhat hydrophobic retain their tensile strength at higher humidities and thereby improve curl retention. However, wave set compositions incorporating a hydrophobic polymer have a number of inherent disadvantages. With these wave set compositions it is generally true that the increase in the desired humidity resistant curl retention is accompanied by increased difficulty in the ability to deposit and remove the polymer film from the hair with aqueous systems.

An object of this invention is to provide a wave setting composition which exhibits improved humidity resistant curl retention capacity and which can be easily deposited on the hair from an aqueous system.

An additional object of this invention is to provide a wave setting composition which exhibits improved humidity resistant curl retention and can be readily removed from the hair by application of a conventional shampoo.

Another object of this invention is to provide a wave setting composition which exhibits improved humidity resistant curl retention and can be used subsequent to shampooing or incorporated into a shampoo base to provide a one-step shampoo/wave set composition.

Other objects and advantages will become readily apparent from the following description and appended claims.

SUMMARY OF THE INVENTION

In accordance with the present invention there is provided an aqueous hair care composition which exhibits excellent wave-setting capacity, which comprises:
(a) From about 0.01 to about 10.0 weight percent based on the total weight of aqueous composition of a polyelectrolyte complex which is the ionic reaction product of one or more polycationic polymers and one or more polyanionic polymers; and
(b) Water.

Preferably, the polyelectrolyte complex is the reaction product of polycationic polymers having a charge density of no more than 0.004, and most advantageously less than about 0.0015.

It has been discovered that the compositions of this invention exhibit improved humidity resistant curl retention, are useful in a wave set protocol for post shampoo application or, alternatively as shown hereinbelow, can also be incorporated in a shampoo base to provide compositions capable of both cleansing and wave-setting hair in a one step treatment. Advantageously, preferred embodiments thereof may be removed from the hair without difficulty.

Also provided in accordance with the invention are non-irritating shampoo compositions which exhibit excellent cleansing and wave setting properties which comprise:
(a) From about 0.01 to about 10.0 weight percent of a polyelectrolyte complex which is the ionic reaction product of one or more polycationic polymers and one or more polyanionic polymers;
(b) Up to about 30 weight percent of an amphoteric, non-ionic, polar non-ionic, zwitterionic, cationic, anionic surfactants or a combination thereof; an
(c) Water. All weight percents are based on the total weight of the aqueous composition.

DETAILED DESCRIPTION OF THE INVENTION

As an essential ingredient, the compositions of this invention include from about 0.01 to about 10 weight percent, and preferably from about 0.1 to about 2.0 weight percent of a polyelectrolyte complex. The polyelectrolyte complex is the ionic reaction product of one or more polycationic polymers and one or more polyanionic polymers.

Cationic polymers suitable for use in preparing the polyelectrolyte complex should have a "cationic charge density" of not more than 0.004 (molecular weight per charge of 250) and preferably not more than about 0.0015 (molecular weight per charge of about 650) in an aqueous solution. The "cationic charge density" of a polymer as that term is used herein refers to the ratio of the total number of positive charges in the polymer and molecular weight of the polymer, i.e.

$$\text{cationic charge density} = \frac{\text{total number of positive charges}}{\text{molecular weight of the polymer}}$$

Suitable cationic polymers for the purpose of this invention are quaternary nitrogen containing cellulosic ether compounds, hereinafter referred to as QNCC ether compounds. These compounds and their method of preparation are described in detail in U.S. Pat. No. 3,472,840 granted to Stone et al. on October 14, 1965.

Illustrative of a particularly efficacious QNCC ether compound for the purpose of this invention is available from Union Carbide under the Tradename "Polymer JR". This polymer has a molecular weight within the range from 100,000 to 3,000,000. Polymer JR is a cationic cellulose ether having the structure:

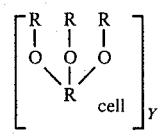

wherein $R_{cell}$ is a residue of an anhydroglucose unit, Y is an integer from 50 to 20,000, and each R individually represents a substituent of the general formula:

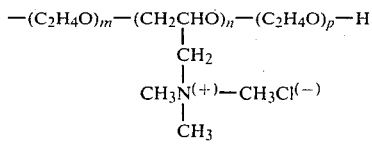

wherein m is an integer from 0 to 10, n is an integer from 0 to 3, and p is an integer from 0 to 10. The average values per anhydroglucose unit are: n is from 0.35 to 0.45 and the sum of m+p is from 1 to 2.

The preferred QNCC ethers are those having viscosities of 50 to 35,000 cps. at 25° C. in 2 percent by weight aqueous solutions, when measured by ASTM D-2364-65 (model LVF Brookfield, 30 rpm., Spindle No. 2), such as, for example, those sold by Union Carbide Corporation under the trademark designation of Polymer JR-125, Polymer JR-400 and Polymer JR-30M, signifying a polymer of the type described having viscosities of 125 cps., 400 cps. and 30,000 cps. respectively.

Also suitable may be cationic polymers such as quaternized vinyl pyrrolidone/aminomethacrylate copolymer; copolymer of adipic acid/dimethylaminohydroxy propyl diethylene triamine; poly(N,N-dimethyl-3,5-methylenepiperidinium chloride; copolymer of acrylamide/poly(N,N-dimethyl-3,5-methylene piperidinium chloride; copolymer of acrylamide/B-methyacryloxy ethyl trimethyl ammonium chloride; quaternized guar gum derivative; polyethylene imine; poly N-(hydroxy-2-propyl) piperazine polyhydroxy amine quaternized with a short chain trialkyl ammonium halide and like polycationic polymers. These cationic polymers and their methods of preparation are well known to those skilled in the art.

Polyanionic polymers suitable for use in preparing the polyelectrolyte complex of the invention may have a molecular weight of from about 2000 to about 3,000,000. The "anionic charge density" of the polyanionic polymer is not critical and may, in general, range from about 0.015 to about 0.0001. The "anionic charge density" as that term is used herein refers to the ratio of the total number of negative charges on the polymer and molecular weight of the polymer, i.e. anionic charge density = $\dfrac{\text{total number of negative charges}}{\text{molecular weight of the polymers}}$ Useful polyanionic polymers for the purpose of this invention are carboxyl-containing polymers, polysulfates, polysulfonates and the like. The preferred polyanionic polymers are carboxyl containing polymers such as polycarboxylic acids and carboxylated cellulose derivatives.

Suitable polycarboxylic acid polymers are those prepared from $\alpha$, -$\beta$-ethylenically unsaturated mono or di carboxylic acids. Exemplary of such monocarboxylic acid polymers are acrylic, methacrylic, ethacrylic, $\alpha$-chloroacrylic, $\beta$-chloroacrylic, $\alpha$-phenylacrylic, vinyl benzoic, crotonic and the like monocarboxylic acid polymers. Illustrative of useful dicarboxylic acid polymers are itaconic, maleic, fumaric, and the like dicarboxylic acid polymers. Polymeric polycarboxylic acid polymers are known compounds that can be prepared by processes known to those skilled in the art.

Also suitable are polycarboxylic acid polymers that are the random copolymers of $\alpha$-$\beta$-unsaturated mono or dicarboxylic acids as hereinabove described, mono or di ethylenically unsaturated hydrocarbons and halosubstituted hydrocarbons that can be either aliphatic or aromatic such as ethylene, butylene, styrene, chlorostyrene, vinyltoluene, ethylstyrene and the like mono olefins and butadiene, isoprene, 2,3-dimethyl butadiene, chloroprene and the like diolefins.

Polycarboxylic acid/olefin copolymers are known compositions that can be conveniently prepared by methods disclosed, for example, in U.S. Pat. Nos. 3,186,844; 3,264,269; 3,264,272; 3,219,619 and references cited therein.

Still another type of carboxyl containing polyanionic polymer useful in the conduct of the invention are carboxylated cellulosic compositions. Illustrative of useful carboxylated cellulosic compositions are sodium carboxymethyl cellulose; hydroxyethylcarboxymethyl cellulose; and the like carboxylated cellulosic compositions. These compositions can be either obtained from commercial sources or prepared by methods well known to those skilled in the art.

The ratio in which the oppositely charged polymers are present in the reaction mixture is not narrowly critical, but optimum results are generally obtained when the polymers are present in stoichiometric proportions. The "stoichiometric ratio" as that term is used herein refers to the ratio of polycationic to polyanionic polymers that react to form the polyelectrolyte complex. The "stoichiometric ratio" may vary from about 5 to 1 to about 1 to 5, depending on the polymers used to prepare the polyelectrolyte complex but preferably will be in the range of from about 2 to 1 to 1 to 2. The "stoichiometric ratio" at which the polymers complex may, but need not, be the same as that required to achieve an equal number of opposing charges. For example, where a QNCC ether compound is complexed with a polycarboxylic acid polymer, the polymeric "stoichiometric ratio" is the same as the ratio of opposing ionic charges. However, in the case of a QNCC ether compound complexed with a carboxylated cellulosic compound in the polymeric "stoichiometric ratio", the resulting complex has two positive charges to one negative charge.

While the "stoichiometric ratio" only refers to the ratio of polycationic to polyanionic polymers that react to form the polyelectrolyte complex, either polyionic polymer may be present in amounts in excess of that stoichiometrically required but such excess polymer will only exist in its free state in the composition and will not participate in the complex.

The hair care composition of the invention can be prepared by simply blending the polyanionic and polycationic polymer reactants with water until a uniform dispersion of the polyelectrolyte complex component is formed. The polyelectrolyte complex component of the composition is insoluble in water but may be readily dispersed therein as formed. The order of addition of the polymer reactants is not critical. Especially good results are obtained, however, when the polyanionic and polycationic polymers are each prepared as separate solutions in water as an initial step with the solutions then mixed together with vigorous agitation until a uniform dispersion of the polyelectrolyte complex reaction product is obtained.

The compositions of this invention may also include as an optional ingredient up to about 30 weight percent of one or more surfactants, i.e. detergents, such as amphototeric, polar non-ionic, non-ionic, zwitterionic, anionic and cationic surfactants or a mixture thereof. This ingredient functions as a lathering and cleansing agent and in certain instances as discussed hereinafter, as a complex solubilizing agent. When this optional ingredient is incorporated into the composition of this invention, the composition is useful as a combination cleansing and wave set agent.

Anionic surfactants, that may be employed in the compositions of this invention are water-soluble soap, non-soap synthetic surfactants or mixtures thereof.

Suitable non-soap anionic organic detergents include, for example, water-soluble salts of organic sulfuric reaction products having in their molecular structure an alkyl group containing from about 8 to about 20 carbon atoms and a radical selected from the group consisting of sulfuric acid ester and sulfonic acid radicals. Important examples of this type of non-soap anionic synthetic detergent, include the sodium, potassium ammonium, or alkanolamine alkyl sulfates, especially those derived by sulfation of higher alcohols produced by reduction of tallow or coconut oil glycerides; sodium or potassium alkyl benzene sulfonates, especially those of the types described by Guenther et. al. in U.S. Pat. No. 2,220,099, granted Nov. 5, 1940 and by Lewis in U.S. Pat. No. 2,477,383, granted July 26, 1949, in which the alkyl group contains from about 9 to about 15 carbon atoms; sodium alkylglyceryl ether sulfonates, especially those ethers of higher alcohols obtained from tallow and coconut oil; sodium coconut oil fatty acid monoglyceride sulfates and sulfonates; sodium salts of sulfuric acid esters of the reaction product of one mole of a higher fatty alcohol (i.e., tallow or coconut oil alcohols) and about 3 moles of ethylene oxide; and others well known in the art, a number being specifically set forth in Byerly, U.S. Pat. Nos. 2,486,921 and 2,486,922.

Additional non-soap anionic organic synthetic detergents which can be used in this invention include the salts of the condensation products of fatty acids with sarcosine, i.e., acyl sarcosinate, wherein the acyl radical has a chain length range from about 10 to 18 carbon atoms.

Preferably, the non-soap anionic organic detergent will be of the high sudsing type as for example, the alkylglyceryl-ether sulfonates, the sulfated fatty alcohols or the alkyl ether ethylene oxide sulfates wherein the ethylene oxide chain averages 3 units, and acyl sarcosinates, all as more fully set forth above. These and the foregoing detergents can be used in the form of their sodium, potassium, ammonium or lower alkanolamine such as triethanolamine salts.

Conventional soaps may also be used as the anionic detergent component of this invention. Suitable soaps include the sodium, potassium, and lower alkanolamine salts of higher fatty acids of naturally occurring vegetable or animal fats and oils. For example, sodium, potassium and triethanolamine salts of fatty acids occurring in coconut oil, soybean oils, castor oil, or tallow, or salts of synthetically produced fatty acids may be used.

A preferred anionic surfactant is the triethanolamine salt of coconut fatty acid, since it is more readily soluble than the salts of higher alkyl chain length fatty acids. Other preferred anionic surfactants include the sodium and potassium salts of coconut fatty acid; sodium lauryl diethoxy sulfate; triethanol amine lauryl sulfate and sodium lauryl diethoxy sulfate; triethanol amine lauryl sulfate and sodium dodecyl sulfate.

Polar non-ionic detergents can be used in compositions of the invention, either by themselves or in conjunction with an amphoteric detergent. By polar non-ionic detergent is meant a detergent in which the hydrophilic group contains a semi-polar bond directly between two atoms, e.g. N→O and P→O. There is charge separation between the two directly bonded atoms, but the detergent molecule bears no net charge and does not dissociate into ions at neutral pH.

Suitable polar non-ionic detergents include openchain aliphatic amine oxides of the general formula $R_1R_2R_3N \rightarrow O$. The arrow is a conventional representation of a semi-polar bond. These compounds are generally prepared by the direct oxidation of the appropriate tertiary amine. When $R_1$ is a much longer chain than $R_2$ and $R_3$, the amine oxides have surface activity. For the purpose of this invention, $R_1$ is an alkyl, alkenyl or monohydroxyalkyl radical having from about 10 to about 16 carbon atoms. Desirable surface active properties are lost if $R_1$ is substantially less than about 10 carbon atoms and the compounds are insufficiently soluble if $R_1$ is greater than about 16 carbon atoms, $R_2$ and $R_3$ are each selected from the group consisting of methyl, ethyl, propyl, ethanol and propanol radicals. Preferably $R_1$ is a dodecyl radical or a mixture of dodecyl with decyl, tetradecyl and hexadecyl such that at least 50% of the radicals are dodecyl radicals. $R_2$ and $R_3$ are preferably methyl radicals. A preferred amine oxide for the purpose of this invention is a dodecyldimethylamine oxide.

Other operable polar non-ionic detergents are the open chain aliphatic phosphine oxides having the general formula $R_1R_2R_3P \rightarrow O$, wherein R is an alkyl, alkenyl or monohydroxyalkyl radical ranging in chain length from 10 to 18 carbon atoms, and $R_2$ and $R_3$ are each alkyl and monohydroxy-alkyl radicals containing from 1 to 3 carbon atoms. A preferred phosphine oxide is dodecyldimethyl phosphine oxides which together with a method of preparation is fully described by Yoke et al. in copending application Ser. No. 173,834, filed Feb. 16, 1962.

As hereinbefore stated, amphoteric detergents can be used in compositions of the invention, either in conjunction with or in place of the polar non-ionic detergents described above. As used herein, the term "amphoteric" is interchangeable with the term "ampholytic". Amphoteric detergents are well known in the art and many operable detergents of this class are disclosed by A. M. Schwartz, J. W. Perry and J. Birch in "Surface Active Agents and Detergents", Interscience Publishers, New York 1958, Vol. 2. Examples of suitable amphoteric detergents include, for example, alkyl betaiminodipropionates, $RN(C_2H_4COOM)_2$; alkyl beta-amino propionates, $RN(H)C_2H_4COOM$; and long chain imidazole derivatives having the general formula:

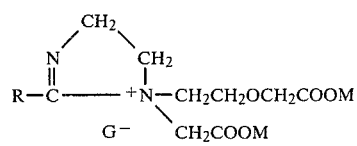

In each of the above formulae R is an acyclic hydrophobic group containing from about 8 to about 18 carbon atoms; G is a hydroxyl, chloride, sulfate or surface active sulfate or sulfonate group and M is a cation to neutralize the charge of the anion. Specific operable amphoteric detergents include the disodium salt of lauroylcycloimidinium-1-ethoxyethionic acid-2-ethionic acid, dodecyl beta alanine, and the inner salt of 2-trimethylamino lauric acid. The substituted betaines and sultaines, such as alkyl ammonio acetates wherein the alkyl radical contains from about 12 to 18 carbon atoms can also be used. The betaine and sultaine types of ampholytic detergents are zwitterionic quaternary ammonium compounds having a general formula:

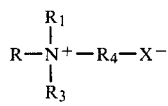

wherein $R_1$ is an alkyl having from about 10 to about 18 carbon atoms, $R_2$ and $R_3$ are each alkyl having from about 1 to about 3 carbon atoms, $R_4$ is an alkylene or hydroxyalkylene having from 1 to 4 carbon atoms, and X is an anion selected from the group consisting of $-SO_3^-$ and $-COO^-$.

Compounds which conform to the above general formula are characterized by the presence of both positive and negative charges which are internally neutralized (i.e. zwitterionic). When the anion X is $-SO_3^-$, these compounds are referred to as "sultaines." The term "betaines" is employed when the anion X is $-COO^-$. The following structural formulae are illustrative of the two types and their inner salt character.

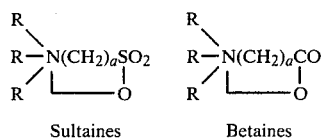

Sultaines        Betaines

When one R in the above formulae is a high weight alkyl having from about 10 to 18 carbon atoms, these compounds are surface active and have good detergency Powers. If the high molecular weight alkyl contains less than about 10 carbon atoms, surface activity and detergency are inadequate. If this group contains more than about 18 carbon atoms, the compounds are not sufficiently soluble to be of utility in this invention. Preferably, the high molecular alkyl will contain from 12 to 16 carbon atoms or a mixture of dodecyl with decyl, tetradecyl, and hexadecyl radicals. A convenient source of a suitable mixture of alkyl groups is the middle cut of coconut fatty alcohol which has the approximate chain length composition: 2%-$C_{10}$, 66%-$C_{12}$, 23%-$C_{14}$, and 9%-$C_{16}$. Particular advantage can be gained by employing betaine or sultaines having an alkyl containing 16 carbon atoms in the compositions of this invention. The alkyl can, of course, contain one or more intermediate linkages such as ether or polyether linkages or non-functional substituents such as hydroxyl or halogen which do not substantially affect the hydrophobic character of the group.

Preferred compounds which fall within the above class include -1(alkyldimethylammonio)acetate, 1-(alkyldimethylammonio)propane-3-sulfonate and 1-(alkyldimethylammonio)-2-hydroxy-propane-3-sulfonate wherein the alkyl contains from 12 to 16 carbon atoms.

Compositions of the invention can contain such other optional ingredients as are desired. These may include, without limitation, ingredients such as organic solvents, such as ethanol; perfumes; sequestering agents, such as tetrasodium ethylenediamine tetraacetate as well as opacifiers, such as ethylene glycol monostearate, which are useful in enhancing the cosmetic properties of shampoo formulations.

Coconut, lauric and myristic mono- and diethanolamides may be used up to about 8% of the formula weight. The compounds serve to aid in the foam stabilization of a polyelectrolyte complex detergent composition; however, they are not essential. Small quantities, up to about 5%, of nonionic surfactants such as ethoxylated higher alcohols, alkyl phenols, and fatty acids may also be included as compatibility agents and to promote rinsing.

Adjustment of the pH of the compositions of the invention, if desired, may be accomplished by the addition of non-toxic acids, such as citric acid or phosphoric acid and bases such as triethanolamine and sodium or potassium hydroxide.

Hair care compositions of this invention which contain components in addition to the polyelectrolyte complex can be prepared by a simple blending of the ingredients, the order of addition not being critical. For example, the polycationic polymer ingredient, such as the QNCC ether, and water are mixed until complete dispersal is achieved followed by the addition of the detergent or detergents until solution occurs. It has been discovered that anionic detergents as herein described will act as a solubilizing agent for the polyelectrolyte complex component. Therefore, when it is desired to prepare the hair care compositions of the invention in the form of a homogeneous solution, the addition of at least 2 percent by weight of an anionic detergent would be advantageous. The polyanionic polymer is now added with stirring until a homogeneous dispersion or solution is achieved. Heat may be applied at this point, if desired, to accelerate dissolution of the polyelectrolyte complex. Other optional ingredients are then added with stirring until a uniform homogeneous mixture is achieved. Acid or alkali is then added for pH adjustment, as desired and as required. Perfume, dyes and preservatives are normally added after pH adjustment.

As had been indicated above, the hair care compositions of the invention comprise a polyelectrolyte complex which is the ionic reaction product of one or more polycationic polymers and one or more polyanionic polymers in water. Compositions of the invention have been found to exhibit improved humidity resistant curl retention when used as a hair composition in a wave set protocol for a post shampoo application or, alternatively, when incorporated in a shampoo detergent base to provide compositions capable of both cleansing and wave setting hair in a one step treatment. The improved humidity resistant curl retention characteristics achieved by the compositions of the invention are, it is believed, attributable to a great extent to the water insoluble nature of the polyelectrolyte complex component which is deposited on the hair. While the polyelectrolyte complex is not water soluble, it has been discovered that the polyelectrolyte complex formed in accordance with the present invention, that is, wherein polycationic polymers having a cationic charged density of no more than 0.004 and preferably less than about 0.0015 can be readily removed from the hair, if desired, by simply rinsing or shampooing the hair with an anionic detergent solution, any of the anionic detergents hereinabove described being suitable for such purpose. Thus, this invention provides hair care compositions which exhibit an improved humidity resitant curl retention capacity and, if desired, can be readily removed from the hair.

The following examples are provided to more clearly illustrate this invention. In the EXAMPLES below the abbreviations employed have the following meanings:

PAA: is polyacrylic acid with a molecular weight per charge of 72 (anionic charge density of 0.014) and a degree of substitution of 1.0, obtained from Colloids, Inc. under the product designation PAA 25.

CMC: is sodium carboxymethyl cellulose having a molecular weight per charge of 310 (anionic charge density of 0.0032) and a degree of substitution of 0.7, obtained from Hercules, Inc., under the product designation L7.

HECMC: is sodium hydroxyethyl carboxymethyl cellulose having a molecular weight per charge of 350 (anionic charge density of 0.0028), a carboxymethyl degree of substitution of 0.7 and a hydroxyethyl degree of substitution of 0.7.

QNCC: is a quaternized hydroxyethyl cellulose having a molecular weight per charge of 700 (cationic charge density of 0.0014), a quaternary degree of substitution of 0.4, and a molecular weight of 400,000 available from Union Carbide Corporation under the Tradename Polymer JR-400.

SURFACTANT I: is a dicarboxylic coconut imidazolinium derivative obtained from Miranol Company Inc. under the Tradename MIRANOL C2MSF.

EXAMPLE I

Polyelectrolyte Complex Used in a Post-Shampoo Application

To evaluate the wave setting efficacy of the compositions of this invention in a post-shampoo application three formulations having the proportion of ingredients listed in Table I, below, were prepared by combining preconcentrates of the individual polymers in aqueous solution with constant stirring at room temperature to form a stable dispersion.

TABLE I

| COMPONENT | FORMULATION AND AMOUNTS BY WEIGHT % | | |
|---|---|---|---|
| | I | II | III |
| QNCC | 1.0 | 1.0 | 1.0 |
| PAA | 0.12 | — | — |
| CMC | — | 0.25 | — |
| HECMC | — | — | 0.25 |
| Water | 98.88 | 98.8 | 98.75 |

Four hair tresses 20.3 cm. long were prepared from 2.4 grams of 25.4 cm virgin brown Italian hair from De Meo Brothers, New York, New York. The tresses were prepared by tieing the root ends and cutting the tips to even length. Each tress was immersed in a 1.0 weight percent solution of a commercial shampoo available from Procter and Gamble, under the Tradename Prell for five minutes at 32° C. The tresses were then rinsed for five minutes under 40° C. tap water. Following cleaning and rinsing, two tresses were treated with four drops of the test formulation, which was distributed through the tresses by gentle combing. The remaining two tresses served as controls. The wet tresses were all curled on 0.5 inch rollers and dried in a forced draft oven at 60° C. for two hours, after which they were allowed to cool for 15 minutes in a chamber maintained at 33% relative humidity. The curlers were then removed from each tress and the tress combed out and placed in a second chamber maintained at 75% relative humidity. The hanging length of each tress was determined immediately and at time intervals over a two hour period using a ruled background within the chamber. From this length L, the % curl was determined at each time using the following equation:

$$\% \text{ Curl} = \frac{20.3 \text{ cm} - L_{cm}}{20.3 \text{ cm}} \times 100$$

The results of this testing are set forth in TABLE II hereinbelow.

TABLE II

| | COMPOSITION I | | | | COMPOSITION II | | | | COMPOSITION III | | |
|---|---|---|---|---|---|---|---|---|---|---|---|
| Time, Min. | Average Tress Length (cm) | | Treated % Curl Control % Curl | Time, Min. | Average Tress Length (cm) | | Treated % Curl Control % Curl | Time, Min. | Average Tress Length (cm) | | Treated % Curl Control % Curl |
| | Treated | Control | | | Treated | Control | | | Treated | Control | |
| 0 | 7.85 | 8.35 | 1.04 | 0 | 7.50 | 7.90 | 1.03 | 0 | 7.25 | 7.90 | 1.05 |
| 15 | 11.40 | 12.10 | 1.08 | 15 | 9.45 | 10.80 | 1.14 | 15 | 9.25 | 9.60 | 1.03 |
| 30 | 13.45 | 15.10 | 1.32 | 30 | 11.75 | 14.15 | 1.46 | 30 | 12.05 | 14.00 | 1.31 |
| 45 | 14.90 | 16.40 | 1.38 | 45 | 13.25 | 15.55 | 1.48 | 45 | 13.40 | 15.70 | 1.50 |
| 60 | 15.55 | 17.40 | 1.63 | 60 | 14.05 | 16.60 | 1.69 | 60 | 14.20 | 16.30 | 1.52 |
| 120 | 16.40 | 18.20 | 1.86 | 120 | 14.95 | 17.30 | 1.77 | 120 | 15.30 | 17.85 | 2.02 |

A leading commercial wave set product, available from Gillette Company, under the Tradename "Dippity-do" was evaluated in the same manner. The results of this test is set forth in Table III, hereinbelow.

TABLE III

| TIME, MIN. | AVERAGE TRESS LENGTH (CM) | | TREATED % CURL CONTROL % CURL |
|---|---|---|---|
| | TREATED | CONTROL | |
| 0 | 6.75 | 8.10 | 1.11 |
| 15 | 8.70 | 10.20 | 1.15 |
| 30 | 11.10 | 12.95 | 1.25 |
| 45 | 13.25 | 14.70 | 1.26 |
| 60 | 14.60 | 15.60 | 1.21 |
| 120 | 15.65 | 16.40 | 1.19 |

In the above test a high ratio of treated % curl to control % curl indicated effective curl retention by the test sample. From a consideration of the treated to control ratios, it is apparent that the composition of this invention imparts hair curl which is more resistant to humidity than that provided by the leading commercial product. This is particularly evident at times exceeding thirty minutes.

To demonstrate the ease of removal of the compositions of this invention, the tresses used in the above evaluations were immersed in a 1.0% solution of a commercial anionic shampoo available from Procter and Gamble under the Tradename Prell for five minutes at 32° C. and then given a five minute rinse in running tap water. The wet tresses were then curled and evaluated as described above. The results of this evaluation are set forth in Table IV hereinbelow.

containing surfactants only. All of the tresses were then curled and tested as described in Example I and the

TABLE IV

| | COMPOSITION I | | | | COMPOSITION II | | | | COMPOSITION III | | |
|---|---|---|---|---|---|---|---|---|---|---|---|
| Time, Min. | Average Tress Length (cm) | | Treated % Curl Control % Curl | Time, Min. | Average Tress Length (cm) | | Treated % Curl Control % Curl | Time, Min. | Average Tress Length (cm) | | Treated % Curl Control % Curl |
| | Treated | Control | | | Treated | Control | | | Treated | Control | |
| 0 | 7.60 | 7.80 | 1.02 | 0 | 7.50 | 8.00 | 1.04 | 0 | 7.65 | 8.00 | 1.03 |
| 15 | 10.00 | 10.70 | 1.07 | 15 | 9.75 | 9.65 | 0.99 | 15 | 9.65 | 9.10 | 0.95 |
| 30 | 12.40 | 13.15 | 1.10 | 30 | 11.80 | 12.10 | 1.03 | 30 | 12.30 | 11.35 | 0.96 |
| 45 | 14.50 | 14.75 | 1.04 | 45 | 13.65 | 14.30 | 1.11 | 45 | 14.05 | 13.75 | 0.96 |
| 50 | 15.40 | 15.70 | 1.07 | 60 | 14.70 | 15.20 | 1.10 | 60 | 15.05 | 15.15 | 1.02 |
| 120 | 17.35 | 17.00 | 0.90 | 120 | 15.75 | 16.70 | 1.26 | 120 | 15.85 | 16.65 | 1.22 |

The results set forth in Table IV demonstrate the nearly complete removal of the composition of this invention from the hair merely by washing with an anionic shampoo.

EXAMPLE II

Polyelectrolyte Complex Used in a Shampoo Application

To evaluate the effect of polyelectrolyte complex in shampoo on curl retention, three representative shampoos were prepared. The shampoo compositions were prepared as follows: The polyanion, in solution, was added with constant stirring to a solution containing the surfactants in the appropriate amounts. To this solution was added an aliquot of the polycation predissolved in water and the entire mixture was stirred to achieve a final, clear solution.

The components of the test shampoo the amounts of each component in weight percent, are set forth in TABLE V hereinbelow.

TABLE V

| COMPONENT | SHAMPOO AND AMOUNT BY WEIGHT PERCENT | | |
|---|---|---|---|
| | I | II | CONTROL |
| QNCC | 0.1 | 0.1 | — |
| PAA | 0.012 | — | — |
| CMC | — | 0.025 | — |
| Miranol C2MSF | 10.0 | 10.0 | 10.0 |
| Triethanolamine lauryl sulfate | 5.0 | 5.0 | 5.0 |
| Water | 84.888 | 84.875 | 85.0 |

Four hair tresses, 20.3 cm long were prepared from 2.4 grams of 25.4 cm virgin brown Italian hair from De Meo Brothers, New York. The tresses were prepared by tieing the root ends and cutting the tips to even length. Two tresses were shampooed manually by massaging 1.0 grams of test shampoo composition into a wetted tress for 30 seconds followed by a 30 second rinse in running tap water at 32° C. The remaining two tresses were treated similarly with the control shampoo results are reported in Table VI.

TABLE VI

| | SHAMPOO I | | | | SHAMPOO II | | |
|---|---|---|---|---|---|---|---|
| Time (Min) | Average Tress Length (cm.) | | Treated % Curl Control % Curl | Time (Min) | Average Tress Length (cm.) | | Treated % Curl Control % Curl |
| | Treated | Control | | | Treated | Control | |
| 0 | 7.25 | 7.40 | 1.01 | 0 | 7.25 | 7.90 | 1.05 |
| 15 | 9.70 | 10.35 | 1.07 | 15 | 10.10 | 10.50 | 1.04 |
| 30 | 12.45 | 13.15 | 1.10 | 30 | 12.30 | 13.00 | 1.10 |
| 45 | 14.05 | 15.00 | 1.18 | 45 | 14.10 | 15.05 | 1.18 |
| 60 | 15.05 | 16.10 | 1.25 | 60 | 15.20 | 16.10 | 1.21 |
| 120 | 16.10 | 17.00 | 1.28 | 120 | 16.75 | 17.30 | 1.18 |

What is claimed is:

1. A method of conditioning hair which comprises applying to said hair an effective amount of a composition which comprises:
   A. from about 0.1 to about 10.0 weight weight percent based on the total weight of the composition of water insoluble polyelectrolyte complex which is the ionic reaction product of one or more polycationic polymers having a cationic charge density of not more than 0.004 and one or more polyanionic polymers; and
   B. water,
   wherein said polyelectrolyte complex provides improved wave-setting capacity over that shown individually by said polycationic or polyanionic polymers.

2. A method according to claim 1 wherein the polycationic polymer used in preparing said polyelectrolyte complex had a cationic charge density not more than about 0.0015.

3. A method according to claim 1 wherein said polyelectrolyte complex is composed of a quaternary nitrogen containing cellulose ether having the structure:

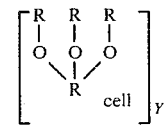

wherein:
R cell is a residue of an anhydroglucose unit;
Y is an integer from 50 to 20,000;
R individually represents a substituent of the general formula:

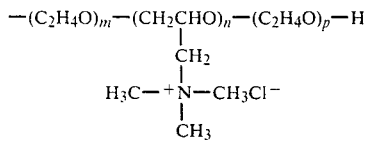

wherein m is an integer from 0 to 10, n is an integer from 0 to 3 and p is an integer from 0 to 10, and a polycarboxylic acid or a carboxylic cellulosic ether.

4. A method according to claim 1 comprising up to about 30 weight percent of an amphoteric, non-ionic, polar non-ionic, zwitterionic, anionic surfactant or mixtures thereof.

5. A method according to claim 2 comprising up to about 30 weight percent of an amphoteric, non-ionic, polar non-ionic, zwitterionic, anionic surfactant or mixtures thereof.

6. A method according to claim 4 wherein said surfactant is sodium lauryl diethoxy sulfate triethanolamine lauryl sulfate, sodium dodecyl sulfate or a combination thereof.

7. A method according to claim 4 wherein said surfactant is a long chain imidazole derivative of the formula:

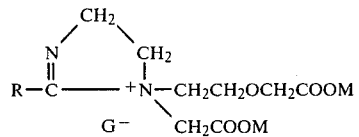

wherein:
R is an acrylic hydrophobic group having from about 8 to about 18 carbon atoms;
G is a hydroxyl, chloride, sulfate or surface active sulfate or sulfonate group;
M is a cation.

* * * * *

UNITED STATES PATENT AND TRADEMARK OFFICE
CERTIFICATE OF CORRECTION

PATENT NO. : 4,299,817

DATED : November 10, 1981

INVENTOR(S) : Roy B. Hannan, III, et al

It is certified that error appears in the above—identified patent and that said Letters Patent is hereby corrected as shown below:

Column 3, lines 5,6,7,8,9,10 please delete:

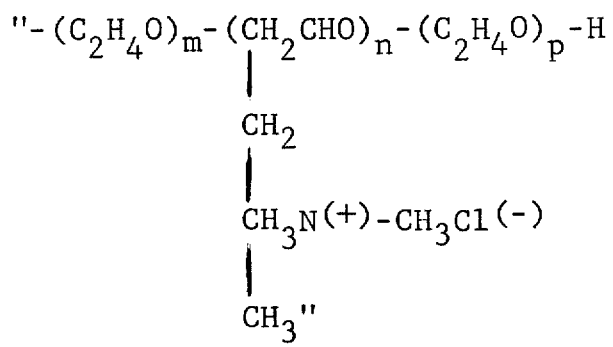

UNITED STATES PATENT AND TRADEMARK OFFICE
CERTIFICATE OF CORRECTION

PATENT NO. : 4,299,817

DATED : November 10, 1981

INVENTOR(S) : Roy B. Hannan, III, et al

It is certified that error appears in the above—identified patent and that said Letters Patent is hereby corrected as shown below:

and insert therefor --

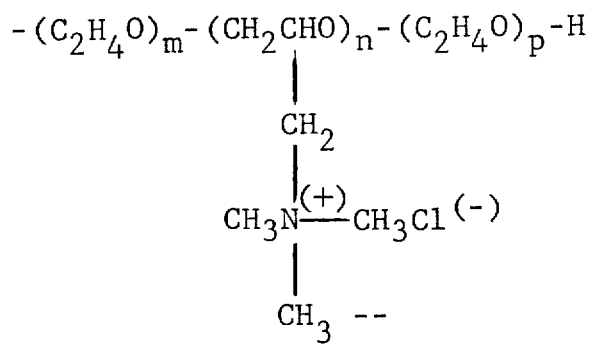

--

[SEAL]

Attest:

Attesting Officer

Signed and Sealed this

Twenty-fifth Day of May 1982

GERALD J. MOSSINGHOFF

Commissioner of Patents and Trademarks